United States Patent [19]
Miyata et al.

[11] Patent Number: 5,154,169
[45] Date of Patent: Oct. 13, 1992

[54] PACING UNIT WITH CATHETER HOLDER

[75] Inventors: Shinichi Miyata; Kiyoshi Takagi, both of Yokohama; Takashi Tsuji, Fujisawa; Masayuki Horikawa, Yokohama; Takashi Kawabata, Hasuda, all of Japan

[73] Assignee: Nippon Zeon Co., Ltd., Tokyo, Japan

[21] Appl. No.: 667,929

[22] Filed: Mar. 12, 1991

[30] Foreign Application Priority Data

Mar. 16, 1990 [JP] Japan .................. 2-26898[U]

[51] Int. Cl.[5] ............................................. A61M 1/00
[52] U.S. Cl. ............................ 128/419 PG; 128/786; 128/419 P
[58] Field of Search ............. 128/419 P, 419 PG, 786, 128/DIG. 26

[56] References Cited
U.S. PATENT DOCUMENTS

| | | | |
|---|---|---|---|
| 3,568,660 | 3/1971 | Crites et al. ......................... 128/786 |
| 3,664,347 | 5/1972 | Harmjanz ............................ 128/786 |
| 3,680,544 | 8/1972 | Shinnick et al. .................... 128/786 |
| 4,112,953 | 9/1978 | Shanker et al. ................. 128/419 P |
| 4,142,532 | 3/1979 | Ware ............................... 128/419 P |
| 4,182,345 | 1/1980 | Grose .............................. 128/419 P |
| 4,248,237 | 2/1981 | Kenny ............................. 128/419 P |
| 4,715,380 | 12/1987 | Harris ............................. 128/419 P |
| 4,721,115 | 1/1988 | Owens ............................... 128/713 |

*Primary Examiner*—William E. Kamm
*Assistant Examiner*—J. Jastrzab
*Attorney, Agent, or Firm*—Armstrong, Nikaido, Marmelstein, Kubovcik & Murray

[57] ABSTRACT

A pacing unit is disclosed. The pacing unit incorporates a catheter with pacing electrodes and leads extending from the pacing electrodes through the body of the catheter, a catheter holder for holding the catheter, and a pacer. Into the pacer, the connector plugs of the leads are plugged with the catheter holder fixedly attached to the pacer by interlocking means consisting of members fitting in respect to each other.

8 Claims, 6 Drawing Sheets

PACING UNIT WITH CATHETER HOLDER

BACKGROUND OF THE INVENTION

1. Field of the Invention

This invention relates to a pacing unit, and more particularly to a cardiac pace maker.

2. Description of the Prior Art

A cardiac pace maker (referred to as a pacer which it is also called so, hereinafter) is an electric device used when arrhythmias occur, to control the heart's rhythm and maintain the normal action of the heart. The pacer, by watching the progress of the heart's action potential wave, can detect an abnormal wave if it occurs, and responds to it by restoring the heart's normal rhythm.

For example, as illustrated in FIG. 10, a pacing catheter 1 with two spaced electrodes 3, 23 at the end is inserted through the vena cava 6 into the heart 7, passing through the right atrium 8 into the right ventricle 9, to at last reach the ventricular apex 9a. The electrodes 3, 23, which thus are positioned at the ventricular apex portion 9a, pick up continuously the action potential of the heart and transmit them via leads 15, 16 running through the catheter lumen to a pacer 5. Upon sensing the absence of the action potential which should be detected at a specified time, immediately the pacer 5 signals via the leads 15, 16 to electrodes 3, 23 which electrically stimulate the heart to pulsate. In FIG. 10, reference characters 10 and 11 designate the left atrium and the left ventricle, respectively.

The pacing unit is constructed of the external pacer 5 disposed apart from the patient's body and the catheter 1 of which the distal end portion is inserted into the heart 7 as stated above. At the proximal end, leads 15, 16 extend out, their connector-plug ends being plugged in the pacer 5. Such construction presents a hazard that the connector plugs can be pulled off the pacer 5, for example, when the patient moves. The pacer 5 itself is usually heavy and large in size (for example, 18 cm long, 8 cm wide and 5 cm high). This may also contribute to the connector plugs being pulled off.

The above-described deficiency reflects, as a potential hazard of medical treatment, a lower reliability of pacing.

OBJECTS AND SUMMARY OF THE INVENTION

It is an object of the present invention to provide a pacing unit that permits pacing at a high reliability.

The present invention therefore is concerned with a pacing unit comprising a catheter with pacing electrodes and leads extending from the pacing electrodes through the body of the catheter, a catheter holder for holding the catheter, and a pacer, the connector plugs of the leads being plugged into the pacer with the catheter holder fixedly attached to the pacer.

Other objects, features and advantages of the invention will appear more fully from the following detailed description thereof taken in connection with the accompanying drawings.

BRIEF DESCRIPTION OF THE DRAWINGS

FIG. 1 is an exploded view in perspective of a pacing unit;

FIG. 2 is a cross-sectional view taken along line II—II of the assembled pacing unit of FIG. 1;

FIG. 3 is a longitudinal sectional view taken along line III—III of the assembled pacing unit of FIG. 1;

FIG. 4 is a longitudinal sectional view which is the same as in FIG. 3 except that it illustrates when the catheter holder is sliding into the position of being fixedly attached to the pacer.

FIG. 5 is a perspective view of the pacing unit when in use;

FIG. 6 is a fragmentary perspective view of the catheter along with the cross-section;

FIG. 7 is a longitudinal sectional view of the end portion of the catheter;

FIG. 8 is an exploded view in perspective of an alternative embodiment of pacing unit;

FIG. 9 is a plane view illustrating the assembled pacing unit of FIG. 8; and

DESCRIPTION OF THE PREFERRED EMBODIMENTS

Embodiments of the present invention will be set forth hereinafter.

FIGS. 1 through 7 illustrate an embodiment of the present invention.

Figure 1:
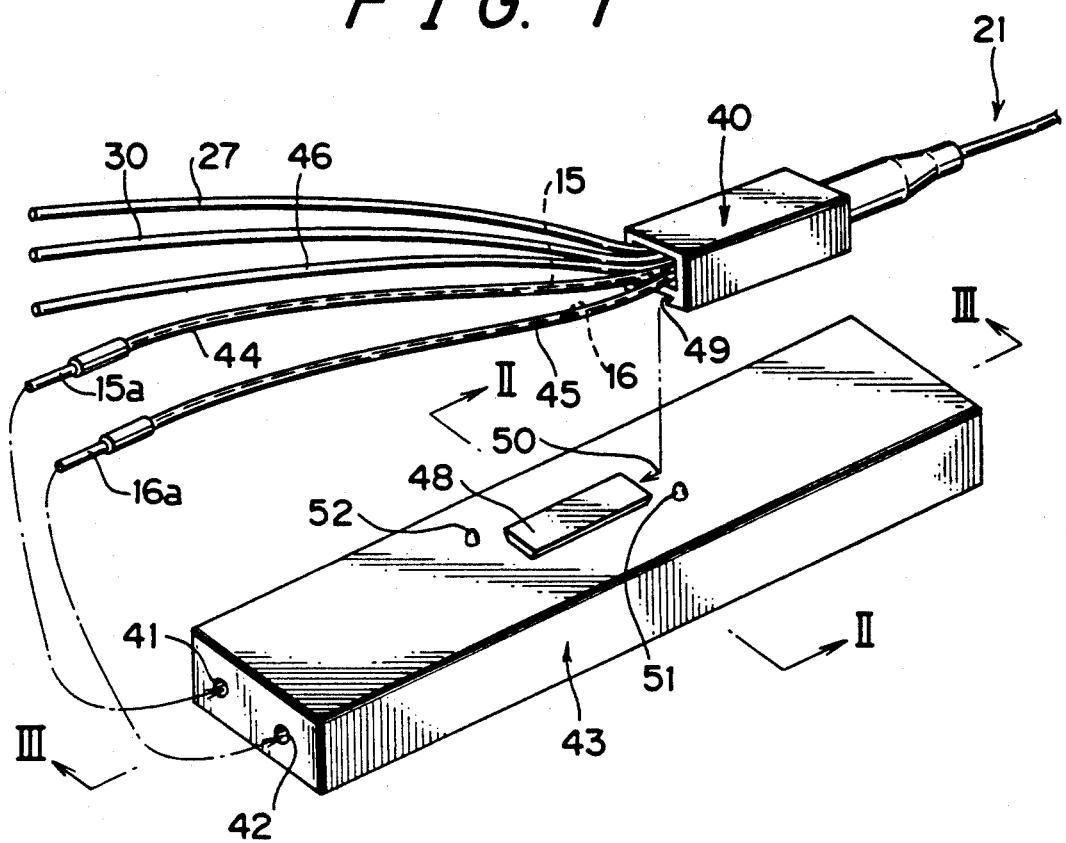
FIGS. 1 through 9 illustrate embodiments of the present invention.
Figure 2:
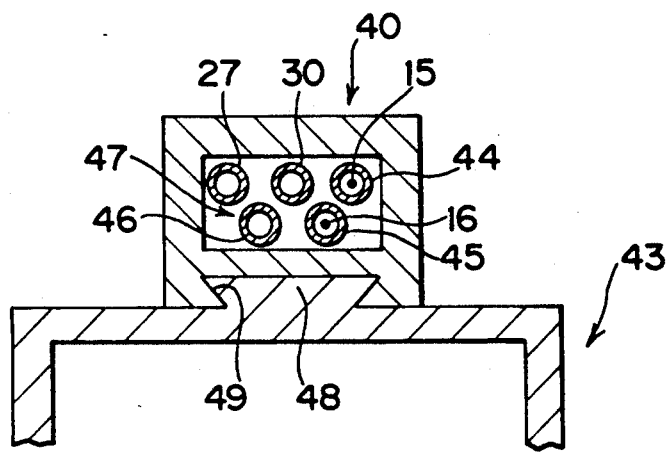
Figure 3:
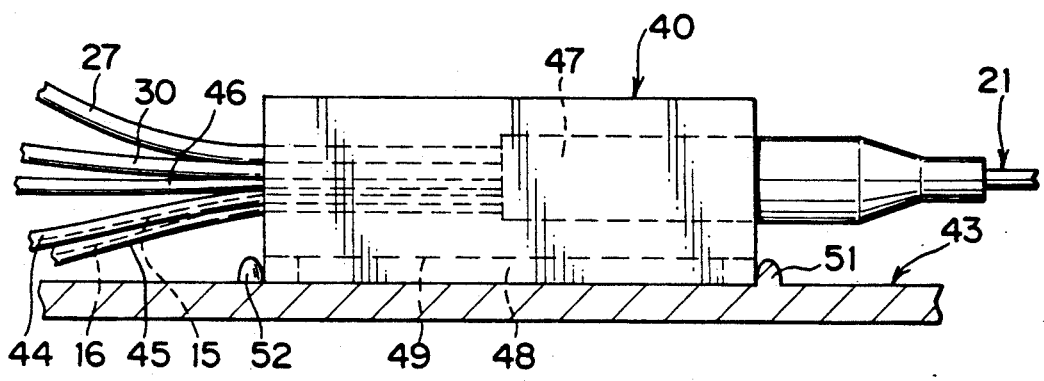
Figure 10:
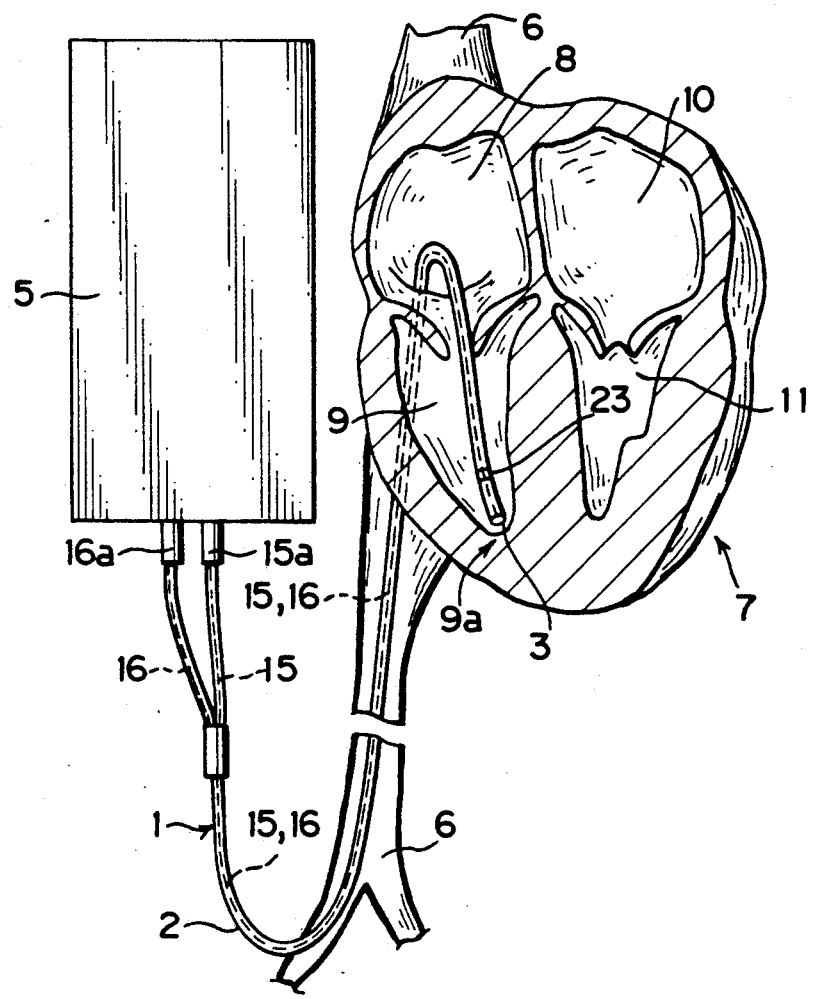
FIG. 10 is a schematic diagram for illustrating a pacing unit in the prior art when in use.

This cardiac pace maker unit embodying the present invention, as shown in FIGS. 1 through 3, is composed essentially of a case-shaped catheter holder 40 carrying a catheter 21 with pacing electrodes similar to electrodes 3, 23 in FIG. 10 and a pacer 43 to the sockets 41, 42 of which connector plug ends 15a, 16a of leads 15, 16 extending from the catheter holder 40 are inserted for electrical connection between the two components, as indicated with dash-and-dot lines. Leads 15, 16 are fitted in tubes 44, 45 (which are small in inner diameter) between the catheter holder 40 and the connector plugs (See FIG. 2). An air tube 27 for a balloon at the end of the catheter 21, a drug injection tube 30, and a pressure-measurement medium tube 46, in addition to the leads 15, 16, extend out of the catheter 21 and are operated conventionally. These tubes 27, 30, 46 together with tubes 44, 45 are introduced into catheter holder 40 and converge at a section indicated by a reference numeral 47 as shown in FIGS. 2 and 3, and communicate with the respective corresponding lumens of the catheter 21 (See FIGS. 6 and 7). For easy understanding, the tubes and the corresponding lumens are designated with the same reference characters. The pacer 43 is basically the same in function as pacer 5 shown in FIG. 10 except the present invention is a relatively miniaturized device adequately small in size (for example, 12 cm long, 2.6 cm wide and 1.2 cm high) and light in weight for attachment to the patient's body.

Figure 4:
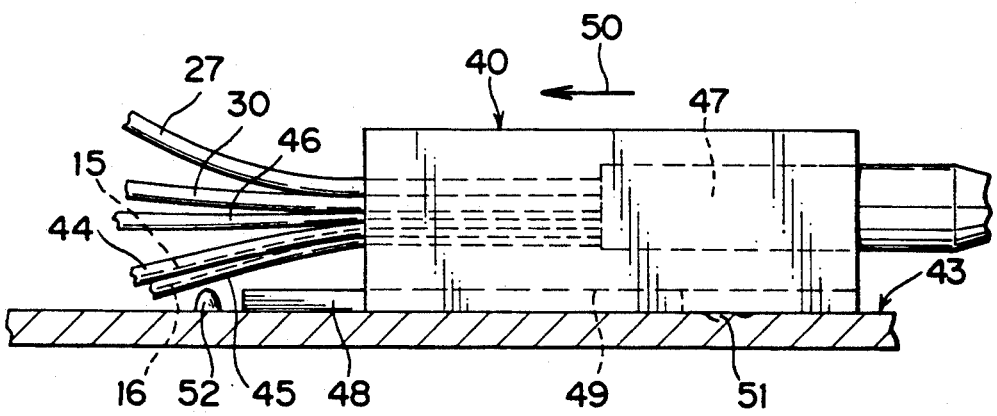

In the pacing unit described above, as shown in FIGS. 1 and 2, a dovetail joint is used as follows: a dove-tail groove (fitting mortise) 49 is provided on the under surface of catheter holder 40, and a flaring rise (tenon) 48 of the corresponding form is provided on the upper surface of pacer 43 so that catheter holder 40 is caused to slide, in the direction of the arrow 50 and as indicated by the dash-and-two-dots line in FIG. 1, into the full-interlocked position between groove 49 and rise 48. A resiliently deformable stop 51 that is provided on the upper surface of pacer 43 is forced to remain compressed under catheter holder 40 when sliding, as shown in FIG. 4, and on termination of the sliding is released to bounce back into shape as shown in FIG. 3. Along with this stop 51 disposed directly behind the catheter holder 40, another stop 52 is provided on the pacer 43 directly in front of it to firmly keep it with the rise 48 and the groove 49 fully interlocked, as illustrated in FIG. 3.

The above-mentioned dovetail joint consisting of rise 48 and groove 49 enables easy attachment of catheter holder 40 to pacer 43, and by cooperation with stops 51, 52, does not allow catheter holder 40 to move up, down, rightwards, leftwards, or any other direction, therefore ensuring firm fixation of the attachment.

This fixed attachment of catheter holder 40 to pacer 43 brings leads 15, 16 extending from catheter holder 40 with connector plugs 15a, 16a plugged in pacer 43 into independent force-relation of catheter 21 and tubes 27, 30, 46. Therefore, even if force such as pulling is unexpectedly given to these, along or in combination, they will not pull out the pacer 43. Pacing is thus always able to continue stably, and with higher reliability.

Figure 5:
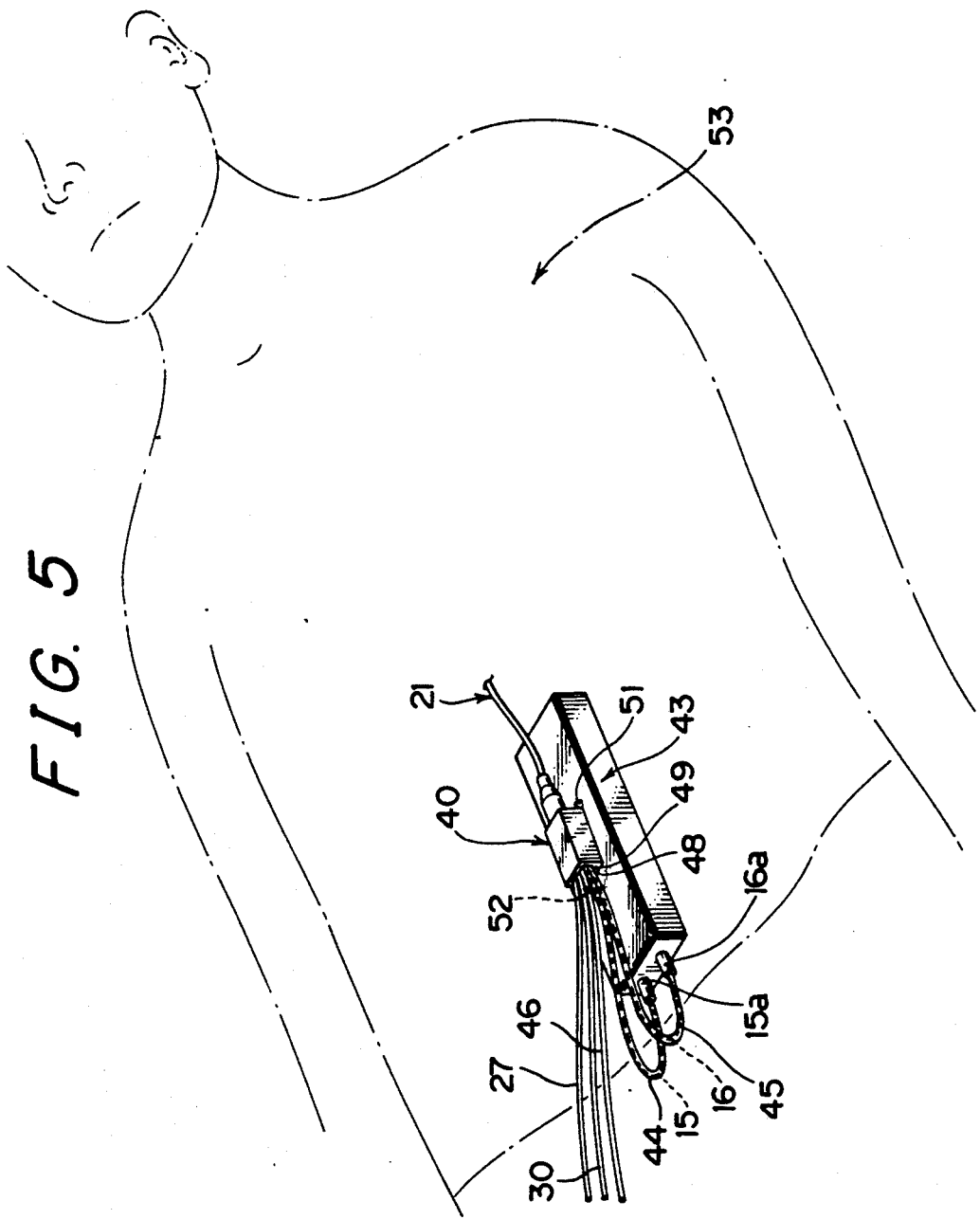

FIG. 5 shows the embodiment of the pacing unit when in use. Pacer 43 is fastened onto the area of a patient 53 including mainly the thoracic part with suitable fastening means. To pacer 43, catheter holder 40 is attached fixedly as described above, and connector plugs are plugged. Then catheter 21 is inserted into the vena cava and further advanced to the specified position in the heart (See FIG. 10).

Figure 6:
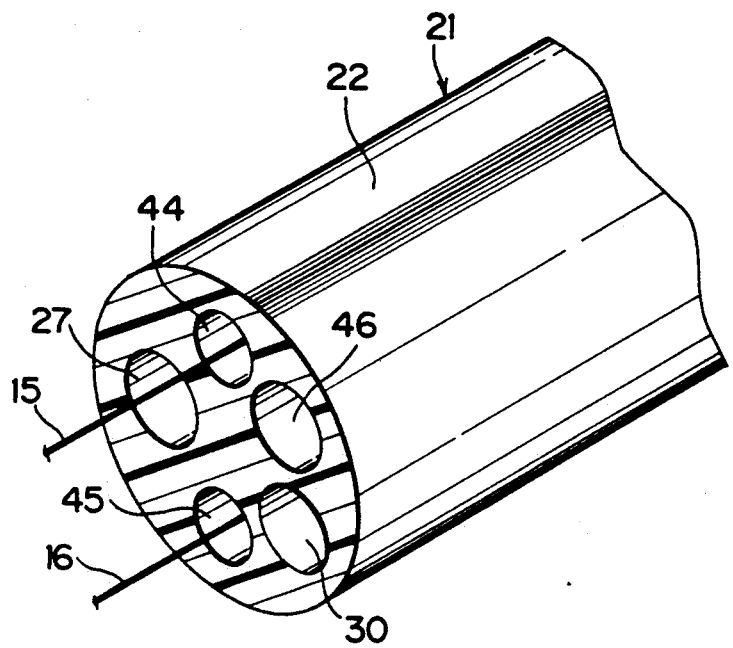
Figure 7:
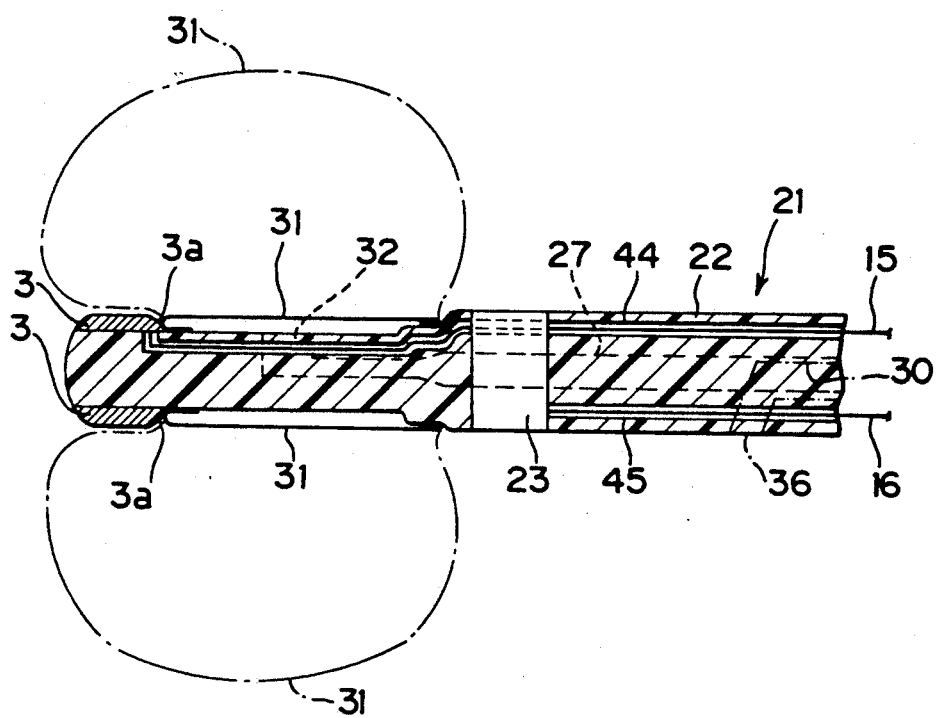

Catheter 21 is provided with 5 axially-running lumens 44, 45, 27, 30 and 46 as shown in FIGS. 6 and 7. Leads 15, 16 extend through lumens 44, 45 to the electrodes at the end, respectively. Air for inflating or deflating the balloon flows through the lumen 27. Injection of, for example, antiarrhythmic is fed through lumen 30, and pressure measurement is conducted through lumen 31. Leads 15, 16 are preferably stranded wires made preferably of a corrosion-proof substance such as stainless steel, gold or platinum. Over the surface of the leads an insulating coating (not shown) may be applied.

Referring to FIG. 7, the catheter 21, the body of which is designated with a reference character 22, has at its leading end portion two spaced electrodes, distal 3 and proximal 23, to which leads 15, 16 extending through lumens 44, 45 are connected. Lumens 27, 30 extend to the distal end portion of catheter 21. Lumen 27 has at its end an air port 32 opening in balloon 31 inflated or deflated (solid and phantom lines define the deflated and inflated, respectively, balloon 31). Lumen 30 has at its distal end an injection outlet 36. Pressure-measurement medium lumen 46 (not shown in FIG. 7) extends through distal electrode 3 and opens at the distal end of the catheter. Distal electrode 3 has a moderately-rounded portion 3a placed in contact with balloon 31 to prevent damage of the balloon from contact.

Figure 8:
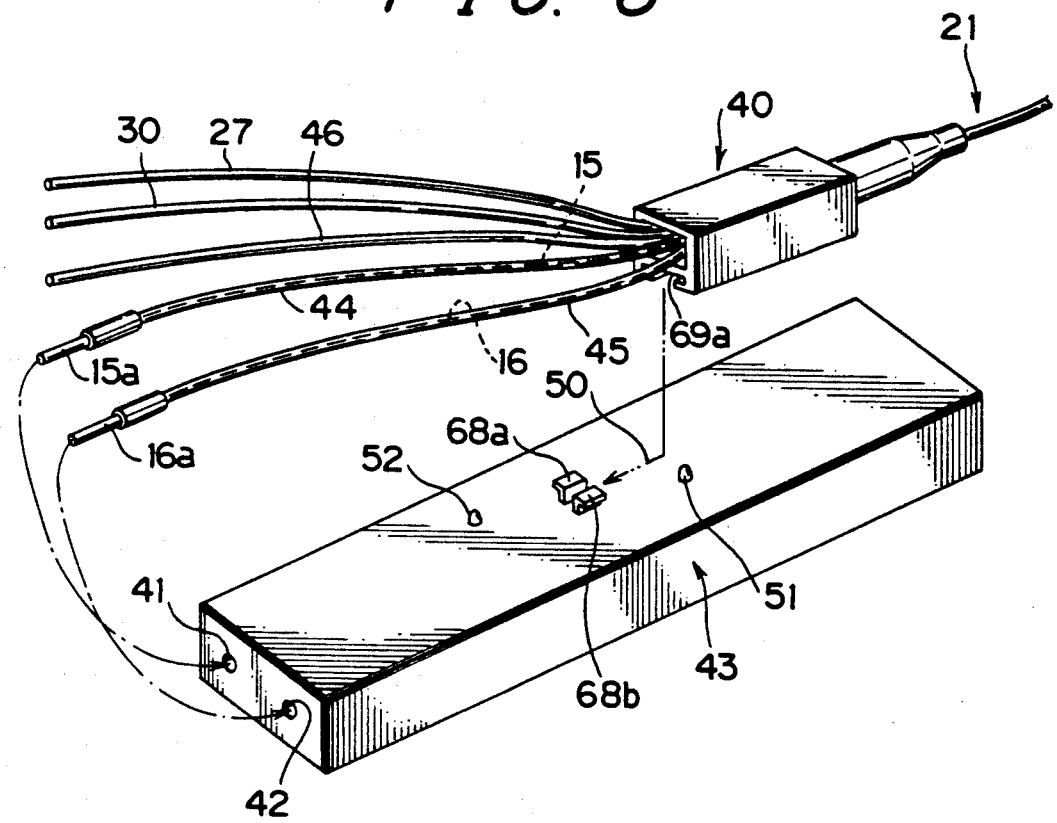
Figure 9:
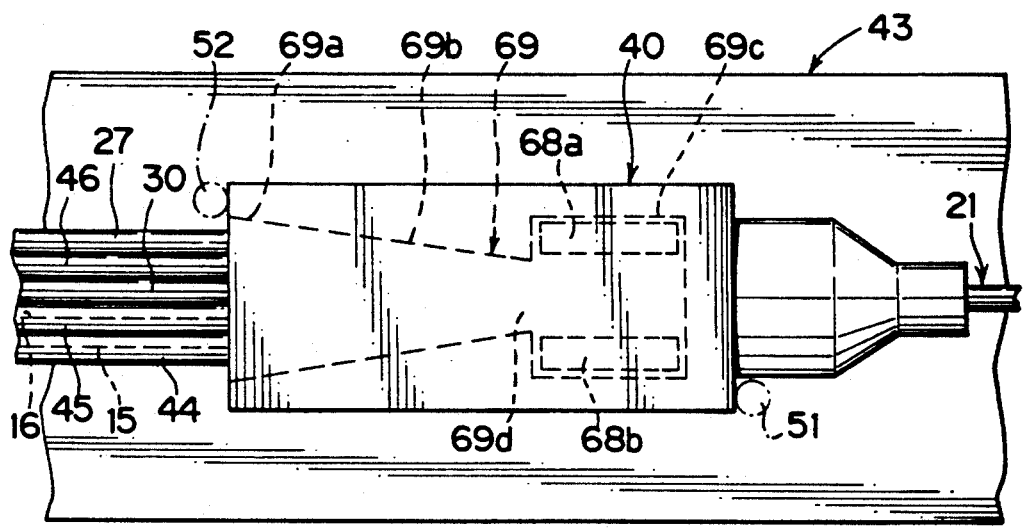

FIGS. 8 and 9 illustrate an alternative embodiment of the present invention.

In this embodiment is used a interlocking mechanism between catheter holder 40 and pacer 43 which can be clicked into position likewise by the slide of catheter holder 40. The construction is as follows: Pacer 43 is provided on the upper surface with a male member, as shown in FIG. 8, consisting of a pair of spaced resilient parts, one an upset L-shaped 68a and the other symmetrical to the former 68b. Catheter holder 40 has a structured bottom which is a female member 69 roughly like a curtain-rail in cross-section as seen from FIG. 8, and consisting, when in a plane view as seen in FIG. 9, of an inward-tapered section 69a, 69b and a rectangular section 69c.

Catheter 40 therefore is interlocked with pacer 43 as follows: male member 68 enters female member 69, and advances inward-tapered section 69a, 69b with parts 68a, 68b moving near to each other. Upon reaching rectangular section 69c, parts 68a, 68b bounce back into shape to be brought into interlock with rectangular section 69c after a narrowed portion 69d as shown in FIG. 9. Thus, the catheter holder 40 gets fixedly attached to pacer 43. In this case, stops 51, 52 indicated with phantom lines having the same effect as mentioned above are not always needed.

This interlocking mechanism can be easily operated for the fixed attachment because female member 69 is structured as shown in the aforesaid pattern when in plane view to allow the male member parts 68a, 68b to enter smoothly into the female member, and to require only a subsequent forced-advance of catheter holder 40. The interlock ensures that catheter holder 40 get firmly locked by the shoulders at the interface 69d between both sections, and more securely does not allow catheter holder 40 to pull off, for example, (unless it is damaged laterally when viewed in FIG. 9). This means that stops 41, 52 are not always needed.

It will be evident that various modifications can be made to the described embodiment without departing from the scope of the present invention.

For example, for the fixed attachment of catheter holder 40 to spacer 43, in the place of the slide fitting or locking mechanism described above, various modifications may be used such as downward fittings screw mechanisms, other lockings, etc. Different shapes and sizes may be used for catheter holder 40 and pacer 43. The construction of catheter 21 is not always limited to those mentioned above. For example, various lumens different in the number and size may be employed in conformance with the object or use. Further instead of a two-electrode catheter in the embodiments described above, those with a single electrode or three or more electrodes may be used.

The present invention, as described above, has the feature that the catheter holder is fixedly attached to the pacer to which the connector plugs of leads from the catheter holder are connected. Thus, the connector plugs are independent of the movement of the catheter even if pulled. The possibility for the connector plugs to pull off is minimized, and thereby reliable pacing is accomplishable always in a stake fashion.

What is claimed is:

1. A pacing unit comprising:
   a catheter having a plurality of pacing electrodes;
   a plurality of leads operatively connected to and extending from the pacing electrodes and extends out of said catheter, at an end opposite said electrodes each of said plurality of leads having a connector plug;
   a catheter holder for holding and enclosing said catheter at a portion where said leads extends out of said catheter; and
   a pacer, said plurality of leads being plugged into said pacer said connector plugs, said catheter holder including means for removably and fixedly attaching said portion to an outer surface of said pacer.

2. A pacing unit according to claim 1 wherein said catheter holder is formed in a shape of a case so as to optimize attachment of said catheter holder to said pacer.

3. A pacing unit according to claim 1 wherein the attaching means of said catheter holder includes means forming a sliding dovetail joint.

4. A pacing unit according to claim 3 wherein the sliding dovetail joint incorporates a tenon member formed on said pacer and a fitting mortise member formed on said catheter holder such that said catheter holder slides into a position of interlocking between the tenon member and the mortise member when attaching to said pacer.

5. A pacing unit according to claim 3 wherein the attaching means of said catheter holder includes a male member formed on the outer surface of said pacer consisting of a pair of resilient formed parts, and a female member formed on said catheter holder and having defined therein first and second sections, the resilient formed parts of the male member resiliently deforming toward each other in the first section of the female member while said catheter holder is sliding in position, and when said catheter holder stops in fixed attachment to said pacer, the resilient formed parts reform back into position to interlock within the second section of the female member.

6. A pacing unit according to claim 1 wherein said pacer includes stops formed on the outer surface of said pacer for securely preventing said catheter holder from detaching from said pacer.

7. A pacing unit according to claim 6 wherein one of the stops on said pacer comprises a resilient projection which compresses while said catheter holder is being attached to said pacer, and when said catheter holder stops in fixed attachment to said pacer, resiliently recovers into shape so as to abut against an end surface of said catheter holder.

8. A pacing unit according to claim 1 wherein said catheter is provided with a plurality of lumens, several of the lumens containing said leads extending therethrough from the pacing electrodes and a remainder of the lumens each having means to communicate to an air tube for a balloon at an end of said catheter, to a drug injection tube and to a pressure measurement medium tube.

* * * * *